United States Patent [19]

Hecht

[11] 4,451,459

[45] May 29, 1984

[54] **BIOLOGICALLY ACTIVE EXTRACTS FROM *MYRCIA FALLAX* (MYRTACEAE) PERU AND METHOD OF OBTAINING SAME**

[75] Inventor: Sidney M. Hecht, Charlottesville, Va.

[73] Assignee: Wofor AG, Switzerland

[21] Appl. No.: 401,306

[22] Filed: Jul. 23, 1982

Related U.S. Application Data

[63] Continuation of Ser. No. 280,086, Jul. 2, 1981, abandoned.

[51] Int. Cl.$^3$ .............................................. A61K 35/78
[52] U.S. Cl. ................................................... 424/195
[58] Field of Search ......................................... 424/195

[56] References Cited

PUBLICATIONS

Cancer Treatment Reports, vol. 60, No. 8, Aug. 1976, pp. 1115-1126.
Chemical Abstract, vol. 76, 138141x and vol. 79, 50703h.

*Primary Examiner*—Albert T. Meyers
*Assistant Examiner*—John W. Rollins
*Attorney, Agent, or Firm*—Sherman & Shalloway

[57] ABSTRACT

This invention provides an extract from the plant *Myrcia fallax* (Myrtaceae) Peru and a method of obtaining same. The extract is obtained by subjecting the plant to a series of extraction steps with a plurality of solvents having different polarities. In each extraction step, the solvent used has a polarity higher than that used in the preceding extraction step. All extraction steps are conducted at room temperature. The extracts have been found to possess biological activity.

9 Claims, No Drawings

BIOLOGICALLY ACTIVE EXTRACTS FROM *MYRCIA FALLAX* (MYRTACEAE) PERU AND METHOD OF OBTAINING SAME

This is a continuation of application Ser. No. 280,086, filed July 2, 1981, abandoned.

BACKGROUND OF THE INVENTION

1. Field of the Invention

This invention relates to materials extracted from plants. More particularly, this invention relates to biologically active materials extracted from the plant *Myrcia fallax* (Myrtaceae) Peru and a method of obtaining such materials.

2. Description of the Prior Art

Crude extracts from plants have been used to treat diseases in humans for centuries. Recently, attempts have been made to extract and isolate pure tumor inhibiting compounds from plants. See, for example, S. M. Kupchan, "Novel plant-derived tumor inhibitors and their mechanisms of action," *Cancer Treat Rep* 60: 1115–1126 (1976). According to Kupchan, to obtain the desired extract, the plant is coarsely ground and subjected to extraction with hot solvent in a Soxhlet apparatus. The temperature at which the extraction is conducted is higher than room temperature, but usually below 40° C. The solvents most often used in such an extraction process include petroleum ether and methanol. The so-obtained crude extract is subjected to further processing (such as fractionation) to yield an extract of higher purity.

In an alternative method, the plant may be extracted in a percolation apparatus with an acceptable solvent. This extraction method is also connected at a temperature higher than room temperature, but usually below 40° C. The crude extract is also subjected to further processing to yield a product of higher purity.

As noted below, it is the normal procedure to extract plants using hot solvents. However, it is the present inventor's belief that extraction under heat is undesirable since some of the biologically active materials in the plant may be destroyed and lose its activity as a result of heating.

Furthermore, in conventional processes, a single solvent is used to extract the plant to produce a crude extract which is then purified. Since a single solvent cannot be expected to be capable of extracting all of the active materials in the plant, it can be reasonably concluded that active materials still remain in the plant after extraction by one solvent. Thus, conventional extraction processes suffer from the disadvantages that part of the active materials to be extracted from the plant is either destroyed by heat or remains unextracted. Clearly, such conventional processes are inefficient.

SUMMARY OF THE INVENTION

The present invention provides biologically active materials extracted from the plant *Myrcia fallax* (Myrtaceae) Peru. These materials are obtained by subjecting the plant to a series of extraction steps with solvents having different polarities, so that in each extraction step a solvent having a polarity (i.e., dielectric constant) higher than that used in the preceding extraction step is utilized. All of the extraction steps are conducted at room temperature. The extract materials have been found to be capable of killing tumor cells derived from human carcinoma of the nasopharynx (KB).

DETAILED DESCRIPTION OF THE INVENTION

According to the present invention, extracts from the plant *Myrcia fallax* (Myrtaceae) Peru is obtained by subjecting the plant to a series of extraction steps using solvents having different polarities (i.e., dielectric constants). The extraction is carried out at room temperature, i.e., from about 20° C. to about 25°C. In each extraction step, the solvent used has a dielectric constant which is higher than that used in the preceding extraction step. The following procedure is used:

(1) The plant, including the twigs, bark and wood portions, are ground into small pieces. The size to which the plant is reduced is not critical since it only affects the length of the extraction period, i.e., the large the size, the longer the extraction time.

(2) The ground plant is subjected to the first extraction step by submerging a weighed portion thereof in a first solvent which is a hydrocarbon solvent having a low polarity. As long as all of the ground plant is completely submerged, the amount of solvent used is not critical. The extraction is conducted for a period of from 1 to 10 days, with the plant-solvent mixture being shaken periodically to ensure that fresh solvent is in contact with the plant. The extraction period is not important since the extraction step is usually repeated with fresh portions of the same solvent. The hydrogen solvent used in this extraction step is the least polar among the solvents used and has a dielectric constant at 20° C. to 25° C. within the range of from about 1.8 to about 2.0. Suitable solvents include pentane, hexane, heptane and petroleum ether, with hexane being preferred.

(3) Thereafter, the solvent is separated from the plant by any convenient method, e.g., decanting. The solvent containing the extract is evaporated to yield a residue, the weight of which is determined. In evaporating the solvent, it is essential that the solvent is not heated above room temperature since heating may destroy some of the biologically materials in the extract. A convenient method of removing the solvent comprises evaporating under a reduced pressure of from about 10 to about 100 mm Hg.

(4) The plant is subjected to at least one additional extraction by repeating steps (2) and (3) with fresh solvents. The extracts obtained in each extraction cycle or step are in the form of a viscous liquid and are pooled, i.e., stored in the same container. The number of cycles to which the plant is subjected to extraction with the hydrocarbon solvent is not limited although it usually varies between 2 and 4. Prior to extraction with another solvent having a higher polarity, as an optional step, the plant is rinsed one or two times with the hydrocarbon solvent which is decanted, with the solvent being permitted to evaporate. Usually, the evaporating is conducted by placing the plant in a ventilated area such as a laboratory hood. After the solvent has evaporated, the plant is ready for extraction with a new solvent having a higher polarity.

(5) After having been extracted with the first solvent, the plant is next extracted with a second solvent having a higher polarity. For this extraction, the second solvent used has a dielectric constant ranging from about 3.5 to about 5.0 at 20° to 25° C. Useful examples of such a solvent include methyl ether, ethyl ether, isopropyl ether and tetrahydrofuran, with ethyl ether being preferred. The amount of solvent used is not critical as long as all of the ground plants are submerged. The extraction is conducted at room temperature for a suitable period, usually from 1 to 10 days, with intermittent agitation.

(6) Thereafter, the solvent is separated from the plant-solvent mixture by any convenient separation method, e.g., decanting. The extract-containing solvent is evaporated at room temperature to obtain a residue, the weight of which is measured. Heating of the solvent during evaporation should be avoided in order to prevent the destruction by heat of biologically active materials in the extract. Typically, the solvent is evaporated under a reduced pressure of from about 10 mm to about 100 mm Hg.

(7) The plant is then subjected to at least one additional extraction by repeating steps (5) and (6) with fresh solvents. The extract obtained in each cycle which are in the form of a viscous liquid are pooled. This extraction of the plant may be repeated for as many times as necessary, although 2 to 4 times are usually sufficient. As an optional step, the plant is rinsed with the solvent of step (5) which solvent is then permitted to evaporate. Thereafter, the plant is ready for extraction with a solvent having a higher polarity.

(8) The plant from step (7) is next extracted with a third solvent having a dielectric constant at 20° to 25° C. ranging from about 15 to about 35, i.e., a solvent having a higher polarity than that of step (5). Examples of suitable solvents include methanol, ethanol, propanol, isopropanol and 1-butanol, with methanol being preferred. The amount of solvent used can be varied, the only requirement being that the plant should be submerged. The length of time for which the extraction is conducted is not critical, usually between 1 to 10 days. The solvent-plant mixture is agitated intermittently.

(9) At the end of the extraction period, the solvent is separated from the plant by any convenient method, e.g., decanting. The extract-containing solvent is evaporated at room temperature to yield a residue, the weight of which is measured. Usually, the solvent is evaporated under a reduced pressure of from about 10 to about 100 mm Hg.

(10) The plant obtained from step (9) is then subjected to additional extraction with fresh solvents by repeating steps (8) and (9), with the extracts obtained in each cycle being pooled. The extracts are in the form of a viscous liquid. This extraction of the plant may be repeated as many times as necessary, although 2 to 4 times have been found to be sufficient. As an optional step, the plant is rinsed once or twice with the solvent of step (8) and dried. The plant is then ready for extraction with a solvent having a still higher polarity.

(11) Prior to extraction with a solvent of higher polarity, as an optional step, the plant is ground in order to reduce its size further. The solvent in this step is water which has a dielectric constant of about 78° to 25° C. In the event that the plant is ground to a fine powder, it may be necessary to add methanol to the mixture in order to cause the powder to submerge. The extraction using water is conducted at room temperature for a suitable period, usually from 1 to 10 days, with intermittent agitation.

(12) At the end of the extraction period, the water is separated from the plant and evaporated at room temperature to reduce the volume thereof. The evaporation can be conducted at a reduced pressure of 10 to 100 mm Hg. The weight of the residue is measured.

(13) The plant from step (12) is subjected to additional extraction with fresh solvents by repeating steps (11) and (12), with the extracts obtained in each cycle being pooled. The extracts may be stored as a liquid or freeze dried to form a powder.

The extracts from steps (4), (7), (10) and (13) are tested individually for their biological activity. More particularly, the effects of the extracts on tumor cells are determined by tissue culture assay. For the present plant, tests are conducted on cells derived from human carcinoma of the nasopharynx (KB). The procedure used in the assay is well known in the art and is described briefly as follows.

As sample of cells is taken from a stock supply and diluted so that the concentration is adjusted to about 100 cells in a circular viewing area of 10 to 15 microns in diameter. The cells are counted to yield an average count prior to the addition of the plant extract.

The extract from step (4) is added to the cells in an ethanol solution and incubated for 48 to 72 hours at 37° C. The concentration of the extract added to the cells is noted. After incubation, the cells are counted to determine the number of live and dead cells. The above procedure is repeated for each of the extracts from steps (7), (10) and (13).

For the present plant, the extracts from step (10) have been found capable of killing KB cells.

As a control, a cell sample is incubated for the same period in culture medium and without the addition of any plant extract. It has been found that after incubation the concentration of the cells is usually doubled, indicating viable cell growth.

The present invention is further illustrated in the following non-limiting example.

EXAMPLE

Three-hundred (300) gm of the ground twigs of *Myrcia fallax* (Myrtaceae) Peru are extracted at room temperature with 1.5 liters of hexane. This extraction step is repeated twice to yield a total of 0.40 gm extract. The twigs are rinsed twice with hexane and dried in a laboratory hood.

The twigs are then extracted at room temperature with 1.5 liters of ethyl ether. This extraction step is repeated twice to yield a total of 0.84 gm extract. The twigs are rinsed twice with ethyl ether and dried in a hood.

The twigs are then extracted at room temperature with 1.5 liters of methanol. This extraction step is repeated twice to yield a total of 9.80 gm extract. The twigs are rinsed twice with methanol and dried in a hood.

The twigs are then extracted with 1.5 liters of water. This extraction step is repeated twice to yield a total of 5.57 gm extract.

Each of the extracts obtained above is tested for its effect on KB cells. The following cell culture assay protocol is used.

To KB cells are obtained from a well-known commercial laboratory. The primary culture is Minimal Essential Medium (MEM) Flo Laboratories, 10% fetal calf serum. Trypsinization is conducted with 0.2% typsin in isotonic NaCl. The cells are counted with 0.1% Tripan Blue. The cells are subcultured in a 5 to 1 split in microtiter plates at $2 \times 10^5$ cells per well. The volume of culture placed in each well is 1 ml. The cells are counted at three locations before the addition of the extract to yield an average cell count.

Each of the four extracts is added to the cells at a concentration of 10 μg/ml as an ethanolic solution. The cells are incubated at 37° C. for 48 hours. Thereafter, the cells are again counted at three locations to provide an average cell count.

The results are summarized in Table 1 which show that the methanol extract (step (10)) is capable of killing KB cells.

TABLE 1

CELL COUNT BEFORE INCUBATION: 100

| SOLVENT | EXTRACTION CYCLES | VOLUME OF SOLVENT LITERS | TOTAL WT. OF EXTRACT GM | CELL COUNT AFTER INCUBATION KB (10 G/ML) | |
|---|---|---|---|---|---|
| | | | | ALIVE | DEAD |
| HEXANE | 3 | 1.5 | 0.40 | 165 | 20 |
| ETHER | 3 | 1.5 | 0.84 | 300 | 20 |
| METHANOL | 3 | 1.5 | 9.80 | 3 | 80 |
| WATER | 3 | 1.5 | 5.57 | 210 | 9 |
| CONTROL | | | | 210 | 8 |

What is claimed is:

1. Biologically active materials from the plant *Myrica fallax*, Myrtaceae, Peru, the materials being produced by the process comprising extracting the twigs, bark and wood portions of the plant with a first solvent having a dielectric constant at 20° to 25° C. of from about 1.8 to about 2.0, a second solvent having a dielectric constant at 20° to about 25° C. of from about 3.5 to about 5.0, and a third solvent having a dielectric constant at 20° to 25° C. of from about 15 to 35, each extraction step being conducted for a period of 1 to 10 days, all extractions steps being conducted at room temperature, and recovering the biologically active materials which are capable of killing tumor cells derived from human carcinoma of the nasopharynx from the extract of the third solvent.

2. The biologically active materials of claim 1 wherein the first solvent is selected from the group consisting of pentane, hexane, heptane and petroleum ether.

3. The biologically active materials of claim 1 wherein the second solvent is selected from the group consisting of methyl ether, ethyl ether, isopropyl ether and tetrahydrofuran.

4. The biologically active materials of claim 1 wherein the third solvent is selected from the group consisting of methanol, ethanol, propanol, isopropanol and l-butanol.

5. A process of obtaining biologically active materials from the plant *Myrica fallax*, Myrataceae, Peru, comprising extracting the twigs, bark and wood portions of the plant with a first solvent having a dielectric constant at 20° to 25° C. of from about 1.8 to 20, a second solvent having a dielectric constant at 20° to about 25° C. of from about 3.5 to about 5.0 and a third solvent having a dielectric constant at 20° to 25° C. of from about 15 to 35, each extraction step being conducted for a period of 1 to 10 days, all of the extraction steps being conducted for a period of 1 to 10 days, all of the extraction steps being conducted at room temperature, and recovering the biologically active materials which are capable of killing tumor cells derived from human carcinoma of the nasopharynx from the extract of the third solvent.

6. The process of claim 5 wherein the first solvent is selected from the group consisting of pentane, hexane, heptane and petroleum ether.

7. The process of claim 5 wherein the second solvent is selected from the group consisting of methyl ether, ethyl ether, isopropyl ether and tetrahydrofuran.

8. The process of claim 5 wherein the third solvent is selected from the group consisting of methanol, ethanol, propanol, isopropanol and l-butanol.

9. The process of claim 5 wherein each extraction step is repeated using fresh portions of the same solvent two to four times.